(12) United States Patent
Jeol

(10) Patent No.: US 10,597,494 B2
(45) Date of Patent: Mar. 24, 2020

(54) THERMOPLASTIC (CO)POLYIMIDES AND SYNTHESIS METHODS

(71) Applicant: Rhodia Operations, Paris (FR)

(72) Inventor: Stéphane Jeol, Cumming, GA (US)

(73) Assignee: Rhodia Operations, Paris (FR)

( * ) Notice: Subject to any disclaimer, the term of this patent is extended or adjusted under 35 U.S.C. 154(b) by 0 days.

(21) Appl. No.: 15/883,726

(22) Filed: Jan. 30, 2018

(65) Prior Publication Data

US 2018/0155498 A1     Jun. 7, 2018

Related U.S. Application Data

(62) Division of application No. 14/345,046, filed as application No. PCT/EP2012/068367 on Sep. 18, 2012, now abandoned.

(30) Foreign Application Priority Data

Sep. 20, 2011 (FR) ..................... 11 58321
Sep. 20, 2011 (FR) ..................... 11 58326
Feb. 23, 2012 (FR) ..................... 12 51644

(51) Int. Cl.
| | |
|---|---|
| C08G 73/10 | (2006.01) |
| C08L 79/08 | (2006.01) |
| D01F 6/74 | (2006.01) |
| C07C 211/63 | (2006.01) |
| C07C 69/76 | (2006.01) |
| C08G 73/00 | (2006.01) |
| C08J 5/00 | (2006.01) |

(52) U.S. Cl.
CPC .......... *C08G 73/1082* (2013.01); *C07C 69/76* (2013.01); *C07C 211/63* (2013.01); *C08G 73/00* (2013.01); *C08G 73/101* (2013.01); *C08G 73/1007* (2013.01); *C08G 73/1028* (2013.01); *C08G 73/1075* (2013.01); *C08J 5/00* (2013.01); *C08L 79/08* (2013.01); *D01F 6/74* (2013.01); *C08J 2379/08* (2013.01); *Y10T 428/2982* (2015.01); *Y10T 442/30* (2015.04); *Y10T 442/40* (2015.04)

(58) Field of Classification Search
CPC . C08L 79/08; C08G 73/1007; C08G 73/1042; C09D 179/08
See application file for complete search history.

(56) References Cited

U.S. PATENT DOCUMENTS 5,512,401 A * 4/1996 Sacripante ......... G03G 9/08766
                                                  430/108.8
9,403,946 B2 * 8/2016 Jeol ................... C08G 73/1075

FOREIGN PATENT DOCUMENTS

EP          0274121       * 12/1987

* cited by examiner

*Primary Examiner* — Gregory Listvoyb
(74) *Attorney, Agent, or Firm* — Thi Diem Dang

(57) ABSTRACT

A salt composition includes at least one ammonium carboxylate salt obtained from: (a) at least one aromatic compound comprising 2 anhydride functional groups and/or its carboxylic acid and/or ester derivatives; and (b) one or more aliphatic diamines in which said aliphatic diamine or diamines are chosen from the diamines of formula (I) $NH_2$—R—$NH_2$ with R being a saturated aliphatic divalent hydrocarbon radical, the two amine functional groups of which are separated by 4 to 6 carbon atoms and 1 or 2 hydrogen atoms of the divalent radical of which are replaced by 1 or 2 methyl and/or ethyl groups; and optionally the diamines of formula (II) $NH_2$—R'—$NH_2$ with R' being a saturated or unsaturated and aliphatic, cycloaliphatic or arylaliphatic divalent hydrocarbon radical, which optionally comprises heteroatoms; and at least one chain-limiting compound chosen from monoamines, monoacids or diacids in the $\alpha,\beta$ positions.

7 Claims, No Drawings

THERMOPLASTIC (CO)POLYIMIDES AND SYNTHESIS METHODS

CROSS-REFERENCE TO RELATED APPLICATIONS

This is a divisional application based on U.S. patent application Ser. No. 14/345,046, filed on Mar. 14, 2014, which is a U.S. national stage entry under 35 U.S.C. § 371 of International Application No. PCT/EP2012/068367 filed Sep. 18, 2012, which claims priority to French Patent Application No. 1251644 filed on Feb. 23, 2012, and French Patent Application No. 1158321, filed on Sep. 20, 2011, and French Patent Application No. 1158326, filed on Sep. 20, 2011. This application claims the benefit and priority of these prior applications and incorporates their disclosures by reference in their entirety.

The present invention relates to novel thermoplastic (co)polyimides and to their processes of synthesis. More specifically, the present invention is targeted at semi-aromatic thermoplastic (co)polyimides obtained by polymerization of at least one aromatic compound comprising two anhydride functional groups and/or its derivatives, in particular carboxylic acid and/or ester derivatives, and at least one specific aliphatic diamine. These (co)polyimides can be converted into plastic articles by various methods, such as extrusion, molding or blow molding.

PRIOR ART

Polyimides, in particular aromatic polyimides, are known for their noteworthy thermal and/or mechanical properties which marks them out in particular for high performance applications in various fields, such as aeronautics or also electronics (printed circuit boards, for example).

Nevertheless, these semi-crystalline aromatic polyimides exhibit a number of disadvantages. They are generally infusible, that is to say that they decompose before melting (at more than 500° C.), and are regarded as thermosets, that is to say that, once formed, they cannot be processed by remelting. Their processing temperatures are generally too high to allow conversion by conventional processes for processing thermoplastic polymers, such as polyamides, in particular extrusion, blow molding or molding. Furthermore, processing at such temperatures can result in significant decomposition of the polyimide matrix and/or in phenomena of colorations harmful to the production of "attractive" parts. In addition, their high melting temperatures hinder or prevent the use of some additives, such as organophosphorus flame retardants or natural fibers, which decompose at such temperatures. Another disadvantage of aromatic polyimides is due to the aromatic diamines, most of which are carcinogens. Due to the points raised above and in particular the difficulties encountered in producing parts made of aromatic polyimides, users frequently turn toward other high performance polymers, such as PEEK (PolyEtherEtherKetone), a semi-crystalline polymer with a melting point of 340° C. and with a glass transition temperature, Tg, of 150° C., which is thus compatible with the processes for the conversion of thermoplastics by remelting.

Aromatic polyimides can be fusible, thus convertible by extrusion or molding techniques, when they comprise aromatic diamines or dianhydrides which are more flexible. For example, such amorphous polyimides with a glass transition temperature Tg of approximately 200° C. are known under the name of polyetherimide, of which Ultem is a commercial name.

Semi-aromatic copolyimides obtained by polymerization of aromatic tetracarboxylic acid with a mixture of aromatic diamine and aliphatic diamine are also known, as described in U.S. Pat. Nos. 5,922,167 and 5,104,966. The content of aliphatic diamine in the starting mixture does not, however, exceed 50%. This condition makes it possible to retain the stiffness of the polymer, the aromatic diamine having the effect of contributing stiffness to the copolyimide obtained, which makes it possible to balance the effect of the aliphatic diamines, which render the polymer supple by lowering the value of the glass transition temperature. These copolyimides are amorphous, the use of two types of diamine disturbing the crystallinity of the polymer.

In addition, the use of aromatic diamines liable to exhibit carcinogenic effects is not satisfactory.

In addition, semi-aromatic polyimides obtained by polymerization of aromatic tetracarboxylic acid and aliphatic diamine are known from U.S. Pat. No. 2,710,853, which describes specific long-chain aliphatic diamines, the two amine functional groups being separated by at least 7 carbon atoms. While these polyimides exhibit an advantageous aptitude for processing, given that they can be shaped at 360° C., on the other hand their glass transition temperature is too low (approximately 135° C.) to compete with other high performance polymers, such as, for example, PEEK, with Tg=150° C. and M.p.=340° C.

Semi-aromatic polyimides thus constitute an advantageous approach to the problems posed as they can be semi-crystalline and/or be convertible by the processing methods known for thermoplastics, due to their melting points compatible with the temperatures for conversion of thermoplastic polymers, that is to say a melting point generally of less than 350° C., while benefiting from an excellent temperature stability.

However, the currently existing semi-aromatic polyimides are not sufficiently effective to compete with the thermoplastic polymers conventionally used in the field of high performance polymers, such as PEEK, having both an M.p. which is high but compatible with the processing equipment and a very high Tg at 150° C., but some of the monomers of which exhibit a high toxicity and/or the processes of synthesis of which can prove to be unsatisfactory in terms of respecting the environment, in particular as a result of the use of toxic monomers.

The objective of the present invention is thus to find novel polymers having good thermal, mechanical and dielectric (insulating) properties and also a good dimensional stability. Furthermore, the polymers must exhibit a high Tg. Advantageously, the polymers will be semi-crystalline with melting points compatible with the temperatures for the conversion of ordinary high performance thermoplastic polymers, a melting point generally of less than 350° C., and thus being convertible by processing methods known for thermoplastics (extrusion, molding, blow molding). In particular, the polymers can be obtained from a great variety of monomers exhibiting a low, indeed even zero, toxicity, which are ecofriendly, which are relatively inexpensive, which are widely available and/or which are easy to synthesize, and the like.

INVENTION

Specific semi-aromatic and thermoplastic (co)polyimides which meet all or some of the abovementioned objectives have just been demonstrated by the applicant company. These (co)polyimides can be prepared by using, as constituent monomers, specific diamines described below.

The present invention thus relates to a semi-aromatic thermoplastic (co)polyimide obtained by polymerization of the following compounds:
(a) at least one aromatic compound comprising 2 anhydride functional groups and/or its derivatives, in particular carboxylic acid and/or ester derivatives;
(b) one or more aliphatic diamines
in which said aliphatic diamine or diamines are chosen from the diamines of formula (I) $NH_2$—R—$NH_2$ with R being a saturated aliphatic divalent hydrocarbon radical, the two amine functional groups of which are separated by 4 to 6 carbon atoms and 1 or 2 hydrogen atoms of the divalent radical of which are replaced by 1 or 2 methyl and/or ethyl groups; and optionally the diamines of formula (II) $NH_2$—R'—$NH_2$ with R' being a saturated or unsaturated and aliphatic, cycloaliphatic or arylaliphatic divalent hydrocarbon radical, which optionally comprises heteroatoms;
or at least one ammonium carboxylate salt obtained from the monomers (a) and (b).

It is thus understood, within the meaning of the present invention, that the repeat units of said (co)polyimide are composed of the compounds (a) and (b), in which the diamines (b) are as defined by the formula (I) and optionally the formula (II).

It is thus possible to reformulate the invention in another way: a semi-aromatic thermoplastic (co)polyimide obtained by polymerization of the following compounds:
(a) at least one aromatic compound comprising 2 anhydride functional groups and/or its carboxylic acid and/or ester derivatives; and
(b) one or more aliphatic diamines
in which at least one aliphatic diamine is chosen from the diamines of formula (I) $NH_2$—R—$NH_2$ with R' being a saturated aliphatic divalent hydrocarbon radical, the two amine functional groups of which are separated by 4 to 6 carbon atoms and 1 or 2 hydrogen atoms of the divalent radial of which are replaced by 1 or 2 methyl and/or ethyl groups;
or at least one ammonium carboxylate salt obtained from the monomers (a) and (b).

The (co)polyimide of the invention can additionally comprise, as other aliphatic diamine (b), one or more diamines of formula (II) $NH_2$—R'—$NH_2$ with R' being a saturated or unsaturated and aliphatic, cycloaliphatic or arylaliphatic divalent hydrocarbon radical, which optionally comprises heteroatoms.

The present invention also relates to an ammonium carboxylate salt obtained from one or more compounds (a) and from one or more aliphatic diamines (b) as defined above or below in the description.

The invention also relates to processes for the preparation of the (co)polyimides according to the invention by polymerization of the monomers (a) and (b) or of the ammonium carboxylate salt obtained from the monomers (a) and (b).

The invention also relates to solid (co)polyimide particles based on (co)polyimide according to the invention, the median diameter D50 of which is less than or equal to 20 mm, preferably between 2 μm and 10 mm.

The invention is also targeted at compositions comprising the (co)polyimide of the invention and fillers and/or additives.

The invention is also targeted at a process for the manufacture of a plastic article employing solid (co)polyimide particles according to the invention, in particular by remelting said particles and then shaping an article, in particular by extrusion, molding or blow molding.

Finally, the invention thus relates to a plastic article obtained from the (co)polyimide according to the invention or from the composition comprising it. It can be a molded part, such as, for example, a part molded by injection molding or a continuous fiber composite, an extruded part, such as, for example, a film, a fiber, a yarn or a filament, or also a blow-molded part. It can also be a part woven or knitted from fibers, yarns or filaments based on (co)polyimide according to the invention.

Definitions

The term "aliphatic diamine" is understood to mean, within the meaning of the present invention, that it concerns diamines, the amine functional groups of which are not covalently bonded to a carbon atom of an aromatic ring, such as a phenyl, for example. On the other hand, if the amine functional group is bonded to a benzyl group, this functional group is covered by the term "aliphatic"; specifically, it is then an arylaliphatic amine.

The term "semi-crystalline" is understood to mean a (co)polyimide exhibiting an amorphous phase and a crystalline phase, for example having a degree of crystallinity of between 1% and 85%. The term "amorphous" is understood to mean a (co)polyimide not exhibiting a crystalline phase detected by thermal analyses (DSC (Differential Scanning Calorimetry) type).

The term "thermoplastic (co)polyimide" is understood to mean a (co)polyimide exhibiting a temperature above which the material softens and melts and which, below this temperature, becomes hard.

The term "median diameter D50" is understood to mean the median which separates the curve for particle size distribution by volume into two parts of equal areas. The particle size analyses can be carried out using a Mastersizer X laser diffraction particle sizer having an extended optical bench from Malvern Instruments S.A., which makes it possible to characterize particle sizes of between 2 and 2000 μm. For the particles of the size between 100 μm and 20 mm, the measurements are carried out by optical microscopy, by measuring the greatest length of 100 particles taken at random from a sample of particles of (co)polyimide. As the distribution is by volume, the median diameter will correspond to 50' of the total volume of the particles. Furthermore, the given median diameter corresponds to the diameter of an equivalent sphere, it being assumed that all the objects have a shape equivalent to a sphere.

When a polyimide is prepared from an ammonium carboxylate salt, the determination of the melting point of the salt is preferably carried out by the measurement of the end temperature of the endotherm measured by Differential Scanning Calorimetry (DSC) using a Perkin Elmer Pyris 1 device, the salt being heated from 20° C. at a rate of 10° C./min.

The determination of the melting point of the (co)polyimide is preferably carried out at the summit of the melting endotherm measured by Differential Scanning Calorimetry (DSC) using a Perkin Elmer Pyris 1 device, the (co)polyimide being heated from 20° C. at a rate of 10° C./min.

The term "particles" is understood to mean, according to the present invention, objects which can take various shapes, such as spherical, substantially spherical, quasispherical, polyhedral, ovoid and/or ellipsoid shapes, and which can exhibit, at the surface, bumps or small cavities forming irregularities, generated by gas bubbles, for example. The particles can be microbeads, beads, aggregates, granules, agglomerates, grains, powder or others. Preference is given in particular to powders, the median diameter D50 of which can generally range from 2 μm to 2000 μm. Granules, the median diameter D50 of which can generally range from 2 mm to 5 mm, are also particularly advantageous according to the invention.

The present invention relates to (co)polyimides obtained from one or more aromatic tetracarboxylic acids and one or more specific aliphatic diamines corresponding to the definition of the invention. The polymers obtained from just one diamine and from just one tetracarboxylic acid are polyimides, generally known as homopolyimides. The reaction between at least 3 different monomers produces a copolyimide. The (co)polyimides can be defined by the molar composition in each constituent monomer.

The (Co)Polyimides

The (co)polyimides of the invention advantageously exhibit a glass transition temperature Tg of greater than 100° C., in particular of greater than 150° C.

When a polymer exhibits a Tg of greater than 100° C., this means that, when the articles made with this polymer are used at a temperature of less than 100° C., the polymer is in its vitreous state, that is to say the state in which it is most rigid. There are a large number of applications in which the temperature of use of these articles does not exceed 100° C. and more particularly 150° C.: for example, a motor vehicle compartment, buildings, and the like. The proportioning of a part is carried out at the temperature at which the article will be used. Thus, if use is made of a polymer for which the Tg is greater than the temperature of use, the calculations take into account the high stiffness of the polymer. With respect to a polymer for which the Tg would be less than the temperature of use, it is thus possible to venture, if appropriate, using less material.

Very particularly, the (co)polyimides of the invention exhibit a Tg of less than or equal to 250° C. This can in particular make possible easier processing.

The (co)polyimides according to the invention can be semi-crystalline and can thus exhibit melting points compatible with the temperatures for conversion of ordinary high performance thermoplastic polymers. The (co)polyimides according to the invention can thus exhibit a melting point M.p. ranging from 100° C. to 350° C., in particular from 150° C. to 350° C.

Advantageously, these (co)polyimides have high crystallization temperatures which make it possible to significantly reduce the production cycle times.

Amorphous polymers exhibit the advantage of being transparent (when they are not formulated), which is important in optics. In order to be able to be used, these polymers absolutely have to exhibit a Tg greater than the temperature of use.

Semi-crystalline polymers exhibit the advantage of retaining mechanical properties beyond their Tg, up to their M.p.

The (co)polyimides obtained are thermoplastics and have the property of not, or only to a slight extent, releasing or absorbing water during subsequent conversion stages, such as pultrusion, extrusion or injection molding. These (co)polyimides can thus exhibit an excellent dimensional stability.

The (co)polyimides according to the invention can have a true density (that is to say, that of a nonporous material) of greater than or equal to 0.9 g/cm$^3$, preferably of greater than or equal to 1 g/cm$^3$. This density can in particular be determined by the ratio of the weight, expressed in grams, to the volume, expressed in cm$^3$, of a solid part made of (co)polyimide according to the invention, of rectangular parallelepipedal shape and of dimensions length (l)×width (w)×thickness (t). The measurement of the density is carried out at ambient temperature, typically at 23° C.

Monomers

The Compounds (a)

The compounds (a) preferably carry carboxylic acid functional groups in positions such that they make it possible to form two acid anhydride functional groups on one and the same molecule (by a dehydration reaction). The compounds (a) generally exhibit two pairs of carboxylic acid functional groups, each functional group pair being bonded to an adjacent carbon atom, in the α and β positions.

The tetracarboxylic acid functional groups can be obtained from acid dianhydrides by hydrolysis of the anhydride functional groups. Examples of acid dianhydrides and of tetracarboxylic acids, derived from the dianhydrides, are described in the patent U.S. Pat. No. 7,932,012.

The compounds (a) of the invention can also carry at least one other functional group. This group can in particular be chosen from the —SO$_3$X group, with X=H or a cation, in particular Na, Li, Zn, Ag, Ca, Al, K and Mg, the hydroxyl —OH group, the ketone C=O group and others —O—.

The aromatic compounds comprising 2 anhydride functional groups are preferably chosen from the group consisting of: pyromellitic anhydride, 3,3',4,4'-biphenyltetracarboxylic dianhydride, 2,3,3',4'-bi-phenyltetracarboxylic dianhydride, 2,2',3,3'-biphenyl-tetracarboxylic dianhydride, 3,3',4,4'-benzophenone-tetracarboxylic dianhydride, 2,2',3,3'-benzophenone-tetracarboxylic dianhydride, 1,2,5,6-naphthalenetetra-carboxylic dianhydride, 2,3,6,7-naphthalenetetra-carboxylic dianhydride, 2,2'-bis(3,4-dicarboxyphenyl)-hexafluoropropanetetracarboxylic dianhydride, 4,4'-oxydiphthalic dianhydride, 2,2-bis(3,4-dicarboxyphenyl) sulfone dianhydride, bisphenol A dianhydride, 3,4,9,10-perylenetetracarboxylic dianhydride and their mixtures.

The preferred aromatic compounds comprising 2 anhydride functional groups are chosen from pyromellitic anhydride, 3,3',4,4'-biphenyltetracarboxylic dianhydride and their mixtures. These compounds, in combination with the diamines (b) of the invention, exhibit the advantage of giving semi-crystalline thermoplastic (co)polyimides having a Tg of greater than 150° C.

Among the abovementioned dianhydrides, pyromellitic anhydride is particularly advantageous, in particular as it is easy to process, relatively inexpensive, widely available and easy to synthesize.

The aromatic compounds comprising carboxylic acid functional groups, in particular derived from the 2 anhydride functional groups, are preferably selected from the group consisting of: pyromellitic acid, 3,3',4,4'-biphenyltetracarboxylic acid, 2,3,3',4'-bi-phenyltetracarboxylic acid, 2,2',3,3'-biphenyl-tetracarboxylic acid, 3,3',4,4'-benzophenonetetra-carboxylic acid, 2,2',3,3'-benzophenonetetracarboxylic acid, 1,2,5,6-naphthalenetetracarboxylic acid, 2,3,6,7-naphthalenetetracarboxylic acid, 2,3,5,6-pyridinetetra-carboxylic acid, 3,4,9,10-perylenetetracarboxylic acid, 3,3',4,4'-tetraphenylsilanetetracarboxylic acid, 2,2'-bis(3,4-dicarboxyphenyl)hexafluoropropanetetra-carboxylic acid, 4,4'-oxydiphthalic acid and their mixtures.

Advantageously, the aromatic compounds comprising carboxylic acid functional groups, in particular derived from the 2 anhydride functional groups, are chosen from pyromellitic acid, 3,3',4,4'-biphenyltetracarboxylic acid and their mixtures. These compounds, in combination with the diamines (b) of the invention, exhibit the advantage of giving semi-crystalline thermoplastic (co)polyimides having a Tg of greater than 150° C.

Among the abovementioned tetraacids (or tetracarboxylic acids), pyromellitic acid is particularly advantageous.

Alternatively, the compounds (a) of the invention can be the esters of the dianhydrides or tetraacids obtained by reaction of dianhydride or tetraacid with a monoalcohol, such as methanol, ethanol, propanol and isomers, or butanol and their isomers. These can be monoesters, diesters (or hemiesters), triesters or tetraesters. Diesters are preferred, in particular the diester of pyromellitic acid.

In a particularly preferred embodiment of the invention, the compounds (a) are tetracarboxylic dianhydrides or acids since these compounds exhibit the advantage of not giving off reaction by-products other than water and in particular they do not give off solvents, such as alcohols. In particular, pyromellitic anhydride or pyromellitic acid is preferred.

Advantageously, these preferred compounds (a) (pyromellitic anhydride or pyromellitic acid) represent at least 80 mol % with respect to the combined compounds (a) employed.

The Compounds (b)

According to the invention, the (co)polyimide has as constituent monomer at least one diamine of formula (I) $NH_2$—R—$NH_2$ with R being a saturated aliphatic divalent hydrocarbon radical, the two amine functional groups of which are separated by 4 to 6 carbon atoms and 1 or 2 hydrogen atoms of the divalent radical of which are replaced by 1 or 2 methyl and/or ethyl groups.

They are diamines having a relatively short and branched chain which, surprisingly, in combination with pyromellitic acid or anhydride, 3,3',4,4'-biphenyltetracarboxylic acid or anhydride, and their mixtures, exhibit the advantage of giving semi-crystalline thermoplastic (co)polyimides having a Tg of greater than 150° C. These properties are also obtained with the corresponding esters of the dianhydrides or tetraacids as defined above.

This diamine is advantageously selected from the group consisting of:

1-methyltetramethylene-1,4-diamine, 2-methyltetra-methylene-1,4-diamine, 1,1-dimethyltetramethylene-1,4-diamine, 1,2-dimethyltetramethylene-1,4-diamine, 1,3-dimethyltetramethylene-1,4-diamine, 1,4-dimethyltetramethylene-1,4-diamine, 2,2-dimethyltetramethylene-1,4-diamine, 2,3-dimethyltetramethylene-1,4-diamine, 1-methylpentamethylene-1,5-diamine, 2-methylpentamethylene-1,5-diamine, 3-methylpentamethylene-1,5-diamine, 1,1-dimethylpentamethylene-1,5-diamine, 1,2-dimethylpentamethylene-1,5-diamine, 1,3-dimethylpentamethylene-1,5-diamine, 1,4-dimethylpentamethylene-1,5-diamine, 1,5-dimethylpentamethylene-1,5-diamine, 2,2-dimethylpentamethylene-1,5-diamine, 3,3-dimethylpenta-methylene-1,5-diamine, 2,3-dimethylpentamethylene-1,5-diamine, 2,4-dimethylpentamethylene-1,5-diamine, 2,5-dimethylpentamethylene-1,5-diamine, 1-methylhexamethylene-1,6-diamine, 2-methylhexamethylene-1,6-diamine, 3-methylhexamethylene-1,6-diamine, 1,1-dimethylhexamethylene-1,6-diamine, 1,2-dimethylhexa-methylene-1,6-diamine, 1,3-dimethylhexamethylene-1,6-diamine, 1,4-dimethylhexamethylene-1,6-diamine, 1,5-dimethylhexamethylene-1,6-diamine, 1,6-dimethylhexamethylene-1,6-diamine, 2,2-dimethylhexamethylene-1,6-diamine, 3,3-dimethylhexamethylene-1,6-diamine, 2,3-dimethylhexamethylene-1,6-diamine, 2,4-dimethylhexamethylene-1,6-diamine, 2,5-dimethylhexamethylene-1,6-diamine, 2,6-dimethylhexamethylene-1,6-diamine, 3,4-dimethylhexamethylene-1,6-diamine, 1-ethyltetramethylene-1,4-diamine, 2-ethyltetramethylene-1,4-diamine, 1,1-diethyltetramethylene-1,4-diamine, 1,2-diethyltetramethylene-1,4-diamine, 1,3-diethyltetramethylene-1,4-diamine, 1,4-diethyltetramethylene-1,4-diamine, 2,2-diethyltetramethylene-1,4-diamine, 2,3-diethyltetramethylene-1,4-diamine, 1-ethylpentamethylene-1,5-diamine, 2-ethylpentamethylene-1,5-diamine, 3-ethylpentamethylene-1,5-diamine, 1,1-diethylpentamethylene-1,5-diamine, 1,2-diethylpentamethylene-1,5-diamine, 1,3-diethylpentamethylene-1,5-diamine, 1,4-diethylpentamethylene-1,5-diamine, 1,5-diethylpentamethylene-1,5-diamine, 2,2-diethylpentamethylene-1,5-diamine, 3,3-diethylpentamethylene-1,5-diamine, 2,3-diethylpentamethylene-1,5-diamine, 2,4-diethylpentamethylene-1,5-diamine, 2,5-diethylpentamethylene-1,5-diamine, 1-ethylhexamethylene-1,6-diamine, 2-ethylhexamethylene-1,6-diamine, 3-ethylhexamethylene-1,6-diamine, 1,1-diethylhexamethylene-1,6-diamine, 1,2-diethylhexamethylene-1,6-diamine, 1,3-diethylhexamethylene-1,6-diamine, 1,4-diethylhexa-methylene-1,6-diamine, 1,5-diethylhexamethylene-1,6-diamine, 1,6-diethylhexamethylene-1,6-diamine, 2,2-diethylhexamethylene-1,6-diamine, 3,3-diethylhexamethylene-1,6-diamine, 2,3-diethylhexamethylene-1,6-diamine, 2,4-diethylhexamethylene-1,6-diamine, 2,5-diethylhexamethylene-1,6-diamine, 2,6-diethylhexamethylene-1,6-diamine, 3,4-diethylhexamethylene-1,6-diamine, 1-ethyl-2-methyltetramethylene-1,4-diamine, 1-methyl-2-ethyltetramethylene-1,4-diamine, 1-methyl-3-ethyltetramethylene-1,4-diamine, 1-ethyl-3-methyl-tetramethylene-1,4-diamine, 1-methyl-4-ethyltetra-methylene-1,4-diamine, 1-methyl-1-ethyltetramethylene-1,4-diamine, 2-methyl-2-ethyltetramethylene-1,4-diamine, 1-ethyl-2-methylpentamethylene-1,5-diamine, 1-methyl-2-ethylpentamethylene-1,5-diamine, 1-methyl-3-ethylpentamethylene-1,5-diamine, 1-ethyl-3-methylpentamethylene-1,5-diamine, 1-methyl-4-ethylpentamethylene-1,5-diamine, 1-ethyl-4-methylpentamethylene-1,5-diamine, 1-methyl-5-ethylpentamethylene-1,5-diamine, 1-methyl-1-ethylpentamethylene-1,5-diamine, 2-methyl-2-ethylpentamethylene-1,5-diamine, 3-methyl-3-ethylpenta-methylene-1,5-diamine, 1-ethyl-2-methylhexamethylene-1,6-diamine, 1-methyl-2-ethylhexamethylene-1,6-diamine, 1-methyl-3-ethylhexamethylene-1,6-diamine, 1-ethyl-3-methylhexamethylene-1,6-diamine, 1-methyl-4-ethylhexa-methylene-1,6-diamine, 1-ethyl-4-methylhexamethylene-1,6-diamine, 1-methyl-5-ethylhexamethylene-1,6-diamine, 1-ethyl-5-methylhexamethylene-1,6-diamine, 1-methyl-6-ethylhexamethylene-1,6-diamine, 1-methyl-1-ethylhexamethylene-1,6-diamine, 2-methyl-2-ethylhexamethylene-1,6-diamine, 3-methyl-3-ethylhexamethylene-1,6-diamine, and their mixtures.

In an advantageous embodiment of the invention, the diamine of formula I is chosen from 1,1-dimethyltetramethylene-1,4-diamine, 1,2-dimethyltetra-methylene-1,4-diamine, 1,3-dimethyltetramethylene-1,4-diamine, 1,4-dimethyltetramethylene-1,4-diamine, 2,2-dimethyltetramethylene-1,4-diamine, 2,3-dimethyltetramethylene-1,4-diamine, 1-methylpentamethylene-1,5-diamine, 2-methylpentamethylene-1,5-diamine, 3-methylpentamethylene-1,5-diamine, 1-ethyltetramethylene-1,4-diamine, 2-ethyltetramethylene-1,4-diamine, and their mixtures.

More preferably still, the diamine of formula I is 2-ethyltetramethylene-1,4-diamine, 2-methylpenta-methylene-1,5-diamine or a mixture of these.

Preferably, the diamine of formula I is 2-methylpentamethylene-1,5-diamine (RN CAS: 15520-10-2).

In a specific embodiment of the invention, the (co)polyimide can comprise at least one other aliphatic diamine of formula (II) $NH_2$—R'—NH in which R' is a saturated or unsaturated and aliphatic, cycloaliphatic or arylaliphatic divalent hydrocarbon radical optionally comprising heteroatoms.

As explained above, the diamines of formula II of the invention are referred to as aliphatic insofar as the amine functional groups are not covalently bonded to a carbon atom of an aromatic group, such as a phenyl, for example. This is the case, for example, with meta-xylylenediamine or para-xylylenediamine.

In other words, R' does not comprise a primary amine functional group directly bonded to an aromatic ring.

The R' radical generally comprises from 2 to 100 carbon atoms, preferably from 4 to 50 carbon atoms. The R' radical can optionally comprise one or more heteroatoms, such as O, N, P or S. The R' radical can comprise one or more functional groups, such as hydroxyl, sulfone, ketone, ether, secondary amine, tertiary amine or other functional groups.

The diamines can in particular be diamines in the α,ω positions comprising from 4 to 20 methylene groups.

The aliphatic diamines can, for example, be selected from the group consisting of: 1,2-diaminoethane, 1,3-diaminopropane, 1,4-diaminobutane, 1,5-diaminopentane, hexamethylenediamine, 2,2,4- and 2,4,4-trimethyl-hexamethylenediamine, 1,7-diaminoheptane, 1,8-diamino-octane, 2-methyl-1,8-diaminooctane, 2,2,7,7-tetramethyloctamethylenediamine, 1,9-diaminonane, 5-methyl-1,9-diaminononane, 1,10-diaminodecane, 1,11-diaminoundecane, 1,12-diaminododecane, 1,13-diaminotridecane, 1,14-diaminotetradecane and diamines resulting from $C_{36}$ fatty acid dimers known, for example, under the Priamine™ name (reference 1075) sold by Croda.

The cycloaliphatic diamines are, for example, selected from the group consisting of isophoronediamine, 1,3-diaminocyclohexane, 1,4-diaminocyclohexane, and diaminodicyclohexylmethane.

Mention may be made of examples of diamines comprising heteroatoms, such as polyetherdiamines, for example the Jeffamine® and Elastamine® products sold by Huntsman. There exists a variety of polyethers composed of ethylene oxide, propylene oxide or tetramethylene oxide units. The number-average molar mass Mn is between 100 and 5000 g/mol.

Advantageously, when a mixture of several aliphatic diamines (b) is used, 2-methylpentamethylene-1,5-diamine represents at least 60 mol % with respect to the combined diamines (b) employed, preferably at least 80 mol %. According to a particularly preferred embodiment, 2-methylpentamethylene-1,5-diamine is used as sole diamine (b) according to the invention.

According to a specific embodiment of the invention, the (co)polyimide according to the invention is obtained by polymerization of pyromellitic anhydride and 2-methylpentamethylene-1,5-diamine. The polyimide thus obtained is particularly advantageous since it is semi-crystalline and since it exhibits an advantageous M.p./Tg compromise, the two temperatures being sufficiently high while allowing the polyimide to be converted by processes for shaping thermoplastic polymers.

According to a second embodiment of the invention, the (co)polyimide according to the invention is obtained by polymerization of pyromellitic acid, 2-methyl-pentamethylene-1,5-diamine and hexamethylene-1,6-diamine.

According to a third embodiment of the invention, the (co)polyimide according to the invention is obtained by polymerization of pyromellitic acid, 2-methyl-pentamethylene-1,5-diamine and 1,10-decanediamine.

According to another embodiment of the invention, the (co)polyimide according to the invention is obtained by polymerization of 3,3',4,4'-benzophenonetetracarboxylic dianhydride and 2-methylpentamethylene-1,5-diamine.

The Salts

The present invention also relates to an ammonium carboxylate salt obtained from one or more compounds (a) and one or more aliphatic diamines (b) as defined above.

The salt according to the invention can additionally comprise at least one chain-limiting compound chosen from monoamines, monoacids or diacids in the α,β positions such that they can form an anhydride functional group by a dehydration reaction.

Advantageously, the compound of formula IV is chosen from: 1-aminopentane, 1-aminohexane, 1-aminoheptane, 1-aminooctane, 1-aminononane, 1-aminodecane, 1-aminoundecane, 1-aminododecane, benzylamine, ortho-phthalic acid (or 1,2-benzenedicarboxylic acid), acetic acid, propionic acid, benzoic acid, stearic acid or their mixtures.

Preference is given to 1-aminohexane, 1-aminododecane, benzylamine or their mixtures. These compounds have the effect of limiting the molar mass of the (co)polyimide and thus of limiting the melt viscosity of the (co)polyimide, which renders it more easily convertible by remelting in order to produce articles.

The content of chain limiter can range from 0.1% to 10% by number of moles, in particular from 1% to 5% by number of moles, with respect to the total number of moles of monomers, that is to say tetracarboxylic acid, diamine and chain limiter.

The Processes of Synthesis

Several processes for the manufacture of the (co)polyimides according to the invention by polymerization of the monomers (a) and (b) are possible.

It is, for example, possible to carry out a solution (or solvent route) polymerization, in particular by following the conventional routes for the synthesis of polyimides in solvent, for example in 2 stages, passing through the intermediacy of a polyamic acid (PAM).

It is also possible to carry out a melt or solid-state polymerization of mixtures of monomers or starting from precursor salts of these monomers.

Preferably, a synthesis by the solid route will be chosen, as described below.

Finally, another technique, described below under the name of spray drying, can also prove to be highly advantageous for the manufacture of the (co)polyimides according to the invention.

Synthesis in Solution (Passing Through PAM)

The process of the synthesis of the (co)polyimides by the solvent route is a two-stage process which consists in reacting, in a first stage, in a polar aprotic solvent, such as dimethylacetamide, dimethylformamide or cresols, or in N-methylpyrrolidone, an aromatic dianhydride with a diamine in order to form an intermediate known as polyamic acid, which is subsequently converted into (co)polyimide in a second stage by raising the temperature or by a chemical dehydration.

During the first stage, the amines open the anhydride rings and give rise to an acid amide functional group often known as amic acid functional group. The polyamic acid formed is generally soluble in the synthesis solvent and is converted by cyclization into (co)polyimide, which is generally insoluble.

Control of the number-average molar mass can be obtained:
- by use of chain limiters, that is to say molecules chosen from monoamines, monoanhydrides, monoacids or diacids in the α,β positions, such that they can form an anhydride functional group by dehydration reaction; mention may be made, among chain limiters, of phthalic anhydride, 1-aminopentane, 1-aminohexane, 1-aminoheptane, 1-aminooctane, 1-aminononane, 1-aminodecane, 1-aminoundecane, 1-aminododecane, benzylamine, ortho-phthalic acid (or 1,2-benzenedicarboxylic acid), acetic acid, propionic acid, benzoic acid, stearic acid or their mixtures,
- by a stoichiometric imbalance r=[aromatic compounds (a)]/[diamines (b)],
- by the use of branching agents, that is to say molecules with a functionality of greater than 3,
- by the adjustment of the operating conditions for syntheses, such as the residence time, the temperature, the humidity or the pressure, or
- by a combination of these different means.

The stoichiometry can be controlled at any moment of the manufacturing process.

In particular, the stoichiometric imbalance r can range from 0.8 to 1.2.

The content of chain limiter can range from 0.1% to 10% by number of moles, in particular from 1% to 5% by number of moles, with respect to the total number of moles of monomers, that is to say tetracarboxylic dianhydride, diamine and chain limiter.

In this process, catalysts, inert or reactive inorganic fillers (clays, silicas or silica precursors, nanoparticles, and the like), stabilizing agents, mattifying agents or colorants can also be introduced.

For example, in order to manufacture a film made of (co)polyimide, it is possible to pour a polyamic acid solution onto a heating surface. During the heating of the heating surface, the solvent evaporates and cyclization takes place, making it possible to obtain a film made of (co)polyimide.

The (co)polyimide can be soluble or insoluble in the solvent. If the (co)polyimide is not soluble in the solvent, the (co)polyimide can be obtained by heating the polyamic acid solution and precipitate. It can thus be recovered by filtration and drying: a powder is obtained. If the (co)polyimide is soluble in the solvent, it can be recovered in a powder form by precipitation in or with a nonsolvent.

Synthesis by the Molten Route

The syntheses by the molten route involve bringing the monomers or precursors to a temperature:
- greater than the melting point of the (co)polyimide, if the (co)polyimide is semi-crystalline, or
- greater than the glass transition temperature, if the (co)polyimide is amorphous.

The melt polymerization can be carried out starting from:
- a diamine and a dianhydride or its tetraacid or diester or triester or tetraester deriviaties,
- a salt of diamine and a tetraacid or a diester.

Advantageously, the polymerization by the molten route is carried out starting from the salts, which exhibit the advantage of precisely controlling the stoichiometry.

The reaction can be carried out in a synthesis reactor or in an extruder provided with a system for venting the vapors.

Melt polymerizations are described in particular in the patent U.S. Pat. No. 2,710,853 starting from aliphatic diamine and pyromellitic anhydride or diester diacid derivatives of pyromellitic anhydride.

Control of the number-average molar mass can be obtained:
- by use of chain limiters, that is to say molecules chosen from monoamines, monoanhydrides, monoacids or diacids in the α,β positions, such that they can form an anhydride functional group by dehydration reaction; mention may be made, among chain limiters, of phthalic anhydride, 1-aminopentane, 1-aminohexane, 1-aminoheptane, 1-aminooctane, 1-aminononane, 1-aminodecane, 1-aminoundecane, 1-aminododecane, benzylamine, ortho-phthalic acid (or 1,2-benzenedicarboxylic acid), acetic acid, propionic acid, benzoic acid, stearic acid or their mixtures,
- by a stoichiometric imbalance r=[aromatic compounds (a)]/[diamines (b)],
- by the use of branching agents, that is to say molecules with a functionality of greater than 3,
- by the adjustment of the operating conditions for syntheses, such as the residence time, the temperature, the humidity or the pressure, or
- by a combination of these different means.

The stoichiometry can be controlled at any moment of the manufacturing process.

In particular, the stoichiometric imbalance r can range from 1.01 to 1.2. This range is advantageous as it makes it possible to prevent the formation of gels by crosslinking of the amine.

The content of chain limiter can range from 0.2% to 10% by number of moles, in particular from 1% to 5% by number of moles, with respect to the total number of moles of monomers, that is to say tetracarboxylic acid/dianhydride, diamine and chain limiter.

In this process, catalysts, inert or reactive inorganic fillers (clays, silicas or silica precursors, nanoparticles, and the like), stabilizing agents, mattifying agents or colorants can also be introduced.

Synthesis by the Solid Route

The principle of the solid-route synthesis consists in preparing the (co)polyimide at a temperature below the melting point of the (co)polyimide starting from a precursor; T<M.p.(PI).

A novel route for the industrial and efficient preparation of semi-aromatic (co)polyimides has just been demonstrated by the applicant company.

This synthesis is rendered possible by the use of a solid-state polymerization of a solid ammonium carboxylate salt formed from an aliphatic diamine and an aromatic tetracarboxylic acid. The (co)polyimides obtained are thermoplastics, generally semi-crystalline thermoplastics, and have the property of not releasing or absorbing water during the subsequent conversion stages, such as, for example, pultrusion, extrusion or injection molding. The process of the invention makes it possible to obtain powders having controlled particle sizes since the polymerization reaction takes place in the solid state.

Furthermore, the solid-state polymerization makes it possible to avoid the use of solvents which are carcinogenic or harmful to the environment.

Another advantage of the process of the invention is the possibility of carrying out the polymerization at a relatively low temperature, making it possible to avoid thermal decomposition of the salt and of the (co)polyimide formed.

The present invention thus relates to a process for the preparation of (co)polyimides according to the invention comprising at least the following stages:
(a) a salt formed by a reaction between at least one aliphatic diamine and at least one aromatic tetracarboxylic acid is placed in a reactor;
(b) a solid-state polymerization is carried out starting from the salt of stage (a) in order to obtain the (co)polyimide at an absolute pressure of between 0.005 and 1 MPa and at a temperature T which obeys the following relationship:
M.p. of the (co)polyimide to be obtained >T preferably
M.p. of the (co)polyimide to be obtained >T>Tg and more preferably still
M.p. of the salt of stage (a)>T>Tg of the (co)polyimide to be obtained,
and
(c) the solid (co)polyimide particles are recovered.

Stage (a)

During stage (a) of the process, a salt formed by a reaction between at least one aliphatic diamine and at least one tetracarboxylic acid is thus placed in a reactor.

Such a salt can be synthesized in various ways known to a person skilled in the art.

It is possible, for example, to add an aliphatic diamine to a solution comprising the tetracarboxylic acid. It is also possible to dissolve the tetracarboxylic acid in a solvent, such as alcohol, for instance ethanol or methanol, for example, and to do the same for the aliphatic diamine. These two solutions are then mixed with stirring. The ammonium carboxylate salt formed can be insoluble in the solvent used and can thus precipitate. The salt can then be recovered by filtration, washed and dried and optionally milled.

It is also possible to prepare a solution of ammonium carboxylate salt, then to concentrate it under hot conditions and subsequently to cool it. The salt then crystallizes and the crystals are recovered and dried. The solution can be concentrated by evaporation of the solvent, such as water or alcohol, or, according to another process, by addition of tetracarboxylic acid and/or aliphatic diamine. It is also possible to saturate the solution, that is to say to carry out a process which makes it possible to modify the concentration of the salt in the solution to a value compatible with crystallization of the salt. Generally, this concentration is at least equal to and more preferably greater than the saturation concentration of the salt at the temperature under consideration. More specifically, this concentration corresponds to supersaturation of the solution of the salt. It is also possible to operate at a pressure which makes it possible to evaporate the solvent from the solution, such as water or alcohol, in order to saturate the solution and to bring about crystallization. It is also possible to saturate the solution by successive or simultaneous addition of a stream of tetracarboxylic acid and of a stream of diamine to a salt solution.

By way of example, the tetracarboxylic acid is dissolved in alcohol, such as ethanol, for example, in a first medium. The aliphatic diamine is dissolved in alcohol, in another medium, and the two media are subsequently mixed with stirring. The salt obtained precipitates.

At the end of this synthesis, the salt can be in the dry powder form, in the form of a powder dispersed in a solvent, or dissolved in solution. It is possible to recover the salt by filtration, in the case of a precipitate, and to break up the filtration cake, if necessary. In the case where the salt is dissolved in solution, it is possible to recover it by a process of crystallization by concentrating, supersaturating or by causing it to precipitate by addition of a nonsolvent. The crystallized salt can then be recovered by filtration and the filtration cake can be broken up, if necessary. Another process which makes it possible to recover the dispersed particles of dry salt is the atomization of the solution, that is to say in particular an operation of sudden evaporation of the sprayed solvent in the form of fine droplets in order to recover the dispersed salt particles.

Finally, it is possible to screen the size of the salt particles, for example by sieving or milling.

Stage (b)

During stage (b) of the process, a solid-state polymerization is thus carried out starting from the salt of stage (a) in order to obtain the (co)polyimide (I) at an absolute pressure between 0.005 and 1 MPa and at a temperature T which obeys the relationship as described above.

The absolute pressure during stage (b) is preferably between 0.005 MPa and 0.2 MPa.

The temperature during stage (b) is preferably between 100° C. and 250° C.

The solid-state polymerization process can be carried out according to conventional processes known to a person skilled in the art. The fundamental principle of these processes consists in bringing the starting salt, under air or in an inert atmosphere or under vacuum, to a temperature lower than its melting point but sufficient to make possible the polymerization reaction, generally greater than the glass transition temperature of the (co)polyimide. Such a process can thus comprise, in brief:
a) heating the product by conductive diffusion, convective diffusion or radiation,
b) rendering inert by application of vacuum, flushing with a neutral gas, such as nitrogen, CO or superheated steam, or applying an excess pressure,
c) removing the condensation by-product by evaporation and then flushing with the carrier gas or concentrating the gas phase,
d) mechanical stirring or fluidizing of the solid phase with the carrier gas or vibrations may be desirable in order to improve the heat and mass transfers and also to prevent any risk of agglomeration of the divided solid.

Preferably, use is made, in stage b), of a means for keeping the particles of (co)polyimide salt moving in order to prevent aggregation of these particles. To do this, use may be made of mechanical stirring, such as a stirrer, rotating the reactor, or stirring by vibrations, or fluidizing with a carrier gas.

The number-average molar mass Mn of the (co)polyimides can be between 500 g/mol and 50 000 g/mol.

Control of the number-average molar mass can be obtained:
by use of chain limiters, that is to say molecules chosen from monoamines, monoanhydrides, monoacids or diacids in the $\alpha,\beta$ positions, such that they can form an anhydride functional group by dehydration reaction. Examples of chain limiters are phthalic anhydride, 1-aminopentane, 1-aminohexane, 1-aminoheptane, 1-aminooctane, 1-aminononane, i-aminodecane, 1-aminoundecane, 1-aminododecane, benzylamine, ortho-phthalic acid (or 1,2-benzenedicarboxylic acid), acetic acid, propionic acid, benzoic acid, stearic acid or their mixtures,
by a stoichiometric imbalance r=[aromatic compounds (a)]/[diamines (b)],
by the use of branching agents, that is to say molecules with a functionality of greater than 3, by the adjustment of the operating conditions for syntheses, such as the residence time, the temperature, the humidity or the pressure, or by a combination of these different means.

The stoichiometry can be controlled at any moment of the manufacturing process.

In particular, the stoichiometric imbalance r can range from 1.01 to 1.2.

According to a specific embodiment:

chain limiters are added to the salt and/or an excess of one of the monomers is added to the salt, in order to create a stoichiometric imbalance, that is to say in order for r to be different from 1.

According to an alternative form, the chain limiter is added to the preformed salt of stage (a).

According to another alternative form, the chain limiter is also in the salt form; in particular, it forms a salt with the aliphatic diamine and/or with the tetracarboxylic acid. In particular, the chain limiter is present during the formation of the salt of stage (a) and is added at the same time as the entity corresponding to it, for example limiter of acid type with the tetracarboxylic acid and limiter of amine type with the aliphatic amine.

In this second case, the chain limiter makes possible the formation of salt and in particular can be chosen from the above lists, with the exception of the anhydrides.

The content of chain limiter can range from 0.1% to 10% by number of moles, in particular from 1% to 5% by number of moles, with respect to the total number of moles of monomers, that is to say tetracarboxylic acid, diamine and chain limiter.

When a chain limiter is used, the amounts of amines and of acids can be balanced, that is to say that the sum of the amine functional groups is substantially equal to half the sum of the acid functional groups with which they can react. The term "substantially equal" is understood to mean a maximum difference of 1%.

When a chain limiter is used, the amount of amines and of acids can be unbalanced, that is to say that the sum of the amine functional groups is substantially different from half of the sum of the acid functional groups with which they can react. The term "substantially different" is understood to mean a difference of at least 1%.

Catalysts can also be introduced and also inert or reactive inorganic fillers (clays, silicas or silica precursors, nanoparticles, and the like), stabilizing agents, mattifying agents, colorants, and the like.

Use may be made of catalysts, added at any moment of the process, such as, for example, as a mixture with the diamine and/or the tetracarboxylic acid, as a mixture with the salt formed, either in solution or by solid-state impregnation.

Furthermore, there exist applications for which it is necessary for the polymers to be provided in the form of powders. This is the case in particular with laser sintering or processes for the manufacture of continuous fiber composites starting from powders by dusting of fabrics or pultrusion of glass or carbon monofilament, or also other processes. The known technologies for the production of polymer powders require either dissolving a polymer in a solvent and precipitating from a nonsolvent; but this involves the use of toxic and carcinogenic solvents, or melt blending the polymer with an immiscible entity, so as to generate segregation of the desired polymer, or milling polymer granules formulated, which imposes additional micronization and drying stages. Whatever the case cited, the processes are complex and expensive.

Synthesis by Spray Drying

In this route, a solution of the monomers or of a salt of the latter in a solvent, generally water, is prepared. The solution is heated under pressure, which initiates the polymerization reaction. The mixture is subsequently flashed, that is to say that the mixture is subjected to a very rapid return to atmospheric pressure with removal of the water vapor, before being sprayed via a nozzle. An example of such a process is described in the patent U.S. Pat. No. 4,603,193. Polyimide particles are thus obtained, which particles can advantageously be subjected to an additional stage of postcondensation in the solid or liquid phase, so as to increase the number-average molar mass Mn of the (co)polyimides thus obtained up to the desired value.

Compositions

The (co)polyimide of the invention can be used to prepare compositions which are generally obtained by blending different compounds, fillers and/or additives. The procedure is carried out at more or less high temperature and at more or less high shear force, according to the nature of the different compounds. The compounds can be introduced simultaneously or successively. Use is generally made of an extrusion device in which the material is heated, then melted and subjected to a shear force, and conveyed. It is possible, according to specific embodiments, to carry out pre-blendings, under molten or non-molten conditions, before preparation of the final composition. It is possible, for example, to produce a pre-blend in a resin, for example (co)polyimide, so as to produce a master batch.

The invention thus also relates to a process for manufacture of a composition by melt or non-melt blending of solid particles of (co)polyimides according to the invention with reinforcing or bulking fillers and/or impact modifiers and/or additives.

The composition according to the invention can optionally comprise one or more other polymers, such as, for example, polyamides, polyesters or polyolefins.

These other polymers advantageously represent less than 40% by weight, with respect to the weight of the composition.

The composition according to the invention can comprise between 20% and 90% by weight, preferably between 20% and 70% by weight and more preferably between 35% and 65% by weight of (co)polyimide according to the invention obtained by the polymerization process as described above, with respect to the total weight of the composition.

The composition can additionally comprise reinforcing or bulking fillers. The reinforcing or bulking fillers are fillers conventionally used for the preparation of thermoplastic compositions, in particular polyamide-based thermoplastic compositions. Mention may in particular be made of fibrous reinforcing fillers, such as glass fibers, carbon fibers or organic fibers, nonfibrous fillers, such as particulate fillers, lamellar and/or exfoliable or nonexfoliable nanofillers, such as alumina, carbon black, clays, zirconium phosphate, kaolin, calcium carbonate, copper, diatomaceous earth, graphite, mica, silica, titanium dioxide, zeolites, talc or wollastonite, polymeric fillers, such as, for example, dimethacrylate particles, glass beads or glass powder. Preference is given in particular to the use of reinforcing fibers, such as glass fibers.

The composition according to the invention can comprise between 5% and 60V by weight of reinforcing or bulking fillers, preferably between 10% and 40% by weight, with respect to the total weight of the composition.

The composition according to the invention comprising the (co)polyimide as defined above can comprise at least one impact modifier, that is to say a compound capable of modifying the impact strength of a (co)polyimide composition. These impact modifiers preferably comprise functional groups which react with the (co)polyimide. The term "functional groups which react with the (co)polyimide" is understood to mean, according to the invention, groups capable of reacting or interacting chemically with the residual anhydride, acid or amine functional groups of the (co)polyimide, in particular covalently, by ionic or hydrogen interaction or by van der Waals bonding. Such reactive groups make it possible to provide good dispersion of the impact modifiers in the (co)polyimide matrix. Mention may be made, for example, of anhydride, epoxide, ester, amine, carboxylic acid, carboxylate derivative or sulfonate functional groups.

The composition according to the invention can additionally comprise additives generally used in the manufacture of polyimide or polyamide compositions. Thus, mention may be made of lubricants, flame retardants, plasticizers, nucleating agents, UV inhibitors, catalysts, antioxidants, antistats, colorants, mattifying agents, molding aids or other conventional additives.

These fillers, impact-reinforcing agents and/or additives can be added to the (co)polyimide by suitable standard means well known in the field of engineering plastics, such as, for example, during salification, after salification, during the solid-state polymerization or in melt blending.

The (co)polyimide compositions are generally obtained by blending under cold conditions or melt blending the various compounds participating in the composition. The procedure is carried out at more or less high temperature and at more or less high shear force, according to the nature of the different compounds. The compounds can be introduced simultaneously or successively. Use is generally made of an extrusion device in which the material is heated, then melted and subjected to a shear force, and conveyed.

All the compounds can be blended in the molten phase during a single operation, for example during an extrusion operation. It is possible, for example, to blend granules of the polymeric materials and to introduce them into the extrusion device in order to melt them and to subject them to more or less high shearing. It is possible, according to specific embodiments, to carry out pre-blendings, under molten or non-molten conditions, of some of the compounds, before preparation of the final composition.

Applications

The (co)polyimide or the various compositions according to the invention can be used in any shaping process for the manufacture of plastic articles.

The invention thus also relates to a process for the manufacture of plastic articles employing solid (co)polyimide particles according to the invention. Mention may be made, to this end, of various techniques, such as the molding process, in particular injection molding, extrusion, extrusion-blow molding, or also rotational molding, in particular in the motor vehicle, electronics, aeronautical and electricity fields, for example. The extrusion process can in particular be a spinning process or a process for the manufacture of films.

The present invention relates, for example, to the manufacture of articles of impregnated cloths type or continuous fiber composite articles. These articles can in particular be manufactured by bringing together a cloth and particles of (co)polyimide according to the invention in the solid or molten state. The cloths are textile surfaces obtained by assembling yarns or fibers rendered integral by any process, such as, in particular, adhesive bonding, felting, braiding, weaving or knitting. These cloths are also denoted as fibrous or filamentary networks, for example based on glass fibers, carbon fibers or other fibers. Their structure can be random, unidirectional (1D) or multidirectional (2D, 2.5D, 3D or other).

The particles of (cc)polyimides of the invention can in particular be used in processes for the manufacture of articles by selective fusion of polymer powder layers, in particular rapid prototyping by solid-phase sintering using a laser. The manufacture by selective fusion of layers is a process for the manufacture of articles which consists in depositing layers of materials in the powder form, in selectively melting a portion or a region of a layer, and in depositing a new layer of powder and in again melting a portion of this layer, and so on, so as to obtain the desired object. The selectivity of the portion of the layer to be melted is obtained, for example, by virtue of the use of absorbers, inhibitors or masks or through the introduction of focused energy, such as, for example, electromagnetic radiation, such as a laser beam. Preference is given in particular to sintering by addition of layers, particularly rapid prototyping by sintering using a laser.

A specific language is used in the description so as to facilitate understanding of the principle of the invention. Nevertheless, it should be understood that no limitation of the scope of the invention is envisaged by the use of this specific language.

The term "and/or" includes the meanings "and", "or" and all the other possible combinations of the elements connected to this term.

Other details or advantages of the invention will become more clearly apparent in the light of the examples given below purely by way of indication.

EXPERIMENTAL PART

Measurement Standards:

The melting points (M.p.) and the crystallization temperatures on cooling (Tc) of the (co)polyimides are determined by Differential Scanning Calorimetry (DSC) using a Perkin Elmer Pyris 1 device at a rate of 10° C./min. The M.p. and Tc values of the (co)polyimides are determined at the summit of the melting and crystallization peaks. The glass transition temperature (Tg) is determined on the same device at a rate of 40° C./min (when this is possible, it is determined at 10° C./min and specified in the examples). The measurements are carried out after melting the (co)polyimide formed at T>(M.p. of the (co)polyimide+20° C.).

When polyimides are synthesized from salts, the melting point of the salt is determined as the end temperature of the endotherm measured by heating the salt to 10° C./min.

The ThermoGravimetric Analysis (TGA) is carried out on a Perkin Elmer TGA7 device, on a sample of approximately 10 mg, by heating at 10° C./min up to 600° C. while flushing with nitrogen.

The proton NMR analysis is carried out on a Brüker AV500 spectrometer.

The CIE L*a*b* colorimetric analysis is carried out on a Minolta CR-310 chromometer.

Example 1: Preparation of Polyimide PI MPMDPMA from a Tetraacid at 200° C.

2.1693 g (0.0081 mol) of 94.9% pyromellitic acid (PMA) (Sigma-Aldrich) are dissolved in 70 g of pure ethanol in a 100 ml reactor with stirring and while flushing gently with nitrogen. A 5% ethanolic solution comprising 0.9508 g (0.0081 mol) of 99? 2-methylpentane-1,5-diamine (MPMD) is added to this reactor over 1 hour using a syringe driver. 10 ml of ethanol are used to rinse out the syringe driver. The stirred reaction medium is heated to 70° C. and maintained for 2 h 30. The polyimide salt formed precipitates and is recovered by complete evaporation of the ethanol at 60° C. under reduced pressure. The salt powder is white and fine. The melting point of the salt is 245° C.

The salt is subsequently brought to 200° C. while flushing with nitrogen for 25 min in order to obtain the polyimide.

The polyimide is semi-crystalline and exhibits a melting point of 338° C. (enthalpy of fusion ΔHf=36 J/g), a crystallization temperature of 269° C. and a Tg=187° C. Compared with the thermal properties of PEEK, the polyimide PI MPMDPMA exhibits a similar melting point but exhibits the advantage of having a glass transition temperature 37° C. greater than that of PEEK.

It turns out that PI MPMDPMA starts decomposing from 398° C. (1? loss in weight) and reaches 54 loss in weight at 437° C.

Thus, PI MPMDPMA can be converted by remelting between 338° C. and 398° C. without massive decomposition.

Example 2: Preparation of Polyimide PI MPMDPMA from a Tetraacid at 300° C.

The salt of example 1 is heated at 10° C./min up to 300° C. while flushing with nitrogen and is then immediately cooled to ambient temperature.

The thermal properties of the polyimide formed are measured: M.p.=322° C. (enthalpy of fusion ΔHf=38 J/g) and Tc=236° C. The M.p. and Tc temperatures turn out to be lower than those measured on the polyimide prepared according to example 1. It is thus preferable to carry out the polymerization at a temperature lower than the melting point of the salt.

Example 3: Preparation of Polyimide PI MPMDPMA from a Diester Diacid at 200° C.

A pyromellitic anhydride diester-diacid derivative is prepared from the reaction of the pyromellitic anhydride with ethanol. 15 g (0.069 mol) of 99.7% pyromellitic anhydride (RN CAS: 89-32-7) supplied by Lonza are introduced into a round-bottom flask containing 300 ml of anhydrous absolute ethanol (5.14 mol). The reaction medium is brought to reflux for 3 hours. The ethanol opens the anhydride functional groups and produces a pyromellitic anhydride diester-diacid derivative. The product is recovered by evaporation of the excess ethanol in a rotary evaporator. A white powder is obtained. The chemical structure of the diester-diacid derived from pyromellitic anhydride is confirmed by NMR analysis in deuterated DMSO.

A salt of MPMD and of the diester-diacid derived from pyromellitic anhydride is prepared by addition of a solution containing 5 ml of absolute ethanol and 0.272 g (2.34 mmol) of 99% 2-methylpentane-1,5-diamine (MPMD) to a solution containing 5 ml of absolute ethanol and 0.729 g (2.34 mmol) of the pyromellitic anhydride diester-diacid derivative prepared above, at ambient temperature and with stirring. After stirring for two hours at ambient temperature, the precipitate formed is recovered by filtration. The white salt powder is obtained and dried in an oven at 50° C. under vacuum in order to remove any trace of residual ethanol.

The salt exhibits a melting point of 216° C.

The polymerization of the salt is carried out by heating the salt at 200° C. for approximately 30 min while flushing with nitrogen. A polyimide is obtained which has the following thermal properties: M.p.=342° C. (ΔHf=21 J/g), Tc=303° C. and Tg=191° C. It turns out that the crystallization temperature is higher than that of the polyimide of example 1 but also that the enthalpy of fusion is lower.

It is preferable to have a higher enthalpy of fusion, meaning that the polymer is more crystalline.

Example 4: Preparation of Polyimide PI MPMDPMA from a Dianhydride in Solution 1.45 g (6.6 mmol) of 99% pyromellitic anhydride and 20 ml of 1,3-dimethyl-2-imidazolidinone (RN CAS: 80-73-9), as polar aprotic solvent, are introduced into a 50 ml two-necked round-bottom flask equipped with a reflux condenser and with a dropping funnel. The reaction medium is stirred at ambient temperature and then 0.774 g (6.6 mmol) of 99-2-methylpentane-1,5-diamine (MPMD) is added via the dropping funnel. The reaction medium is subsequently brought to 140° C. and is maintained at 140° C. for 1 hour. After cooling, the solution of polyamic acid formed is precipitated from 100 ml of ethanol. The precipitate (orange-colored solid) is recovered by filtration and then brought to 200° C. for 30 min. The polymer obtained is orange-yellow in color and exhibits the following thermal properties: M.p.=339° C., Tc=301° C., Tg=191° C.

Example 5: Preparation of Polyimide PI MPMDPMA in the Presence of a Chain Limiter 35 g (0.1344 mol) of 97.64 pyromellitic acid (PMA) are dissolved in 665 g of pure ethanol in a 2 l reactor with stirring while flushing gently with nitrogen. A solution containing 15.373 g (0.131 mol) of 99% 2-methylpentane-1,5-diamine (MPMD), 0.7074 g (0.00692 mol) of 99% 1-aminohexane and 200 g of ethanol is added to this reactor over 1 hour with a dropping funnel. After introducing the solution into the reactor, 20 ml of ethanol are used to rinse out the dropping funnel. The stirred reaction medium is heated to 70° C. and maintained for 3 h. The polyimide salt formed precipitates and is recovered by complete evaporation of the ethanol at 65° C. under reduced pressure. The salt powder is white and fine.

The salt is subsequently brought to 200° C. for 5 h while flushing with nitrogen in order to obtain the polyimide. A white polyimide powder is obtained: the color of the PI MPMDPMA powder is analyzed. It has the following CIE colorimetric characteristics: $L^*$=94.98, $a^*$=0.42, $b^*$=5.02, which indicates that the powder is very white (slightly yellow powders generally exhibit a $b^*$>10). This polymerization process makes it possible to prevent colorations related either to decompositions or to the presence of residual solvents, as is the case in the polymerizations of polyimides by the molten route, above the melting point of the polyimide, or by the solvent route.

The polyimide powder obtained is analyzed by measurement of the relative solution viscosity in 96' sulfuric acid of a 10 g/l polyimide solution in an Ubbelohde tube with a diameter of 1.03 mm in combination with a Schott viscometer having the reference AVS350 and at a temperature of 25° C. The relative viscosity is 1.77.

Example 6: Study of the Melt Stability of the Polyimide of Example 5

1 g of the polyimide of example 5 is placed in a test tube and rendered inert with nitrogen. The tube is placed in a block heated to 350° C. (above the melting point of the polyimide) for 30 min. After 30 min, the relative viscosity is determined at 1.75, which shows that the viscosity of the polyimide has not changed during its conversion to the molten state for 30 min. It can thus be easily employed by remelting in the form of an object at 350° C. without major decomposition.

Example 7: Injection of the PI MPMDPMA

The polyimide PI MPMDPMA powder of example 5 is injected using a microinjection molding machine in combination with the DSM MIDI 2000 microcompounder (volume 15 cm$^3$) by remelting the polyimide at a temperature of 350° C. (temperature of the barrel) and injection into a mold regulated at 180° C. in order to form rods with dimensions of 90×13×1.6 mm$^3$. The rods are completely opaque and very rigid. A dynamic mechanical analysis in three-point bending (imposed strain of 0.01%, frequency 1 Hz) is carried out on a TA Instrument RSA3 device. At 23° C., the E' modulus is equal to 3.2 GPa and the alpha transition temperature is determined at 193° C. An important point is that the PI MPMDPMA retains its stiffness up to 193° C. since, for example at 150° C., E' is still 2.6 GPa.

A burning test with a flame shows that the test specimens exhibit a good fire resistance.

Example 8: Preparation of the Polyimide PI MPMDODPA from a Tetraacid 4,4'-Oxydiphthalic Acid at 200° C.

97% 4,4'-Oxydiphthalic anhydride (ODPA), purchased from Sigma-Aldrich, is hydrolyzed in hot water at reflux for 2 hours. 100% 4,4'-Oxydiphthalic acid (ODA) is thus recovered by evaporation of the water and drying.

1.54 g (0.0044 mol) of 4,4'-oxydiphthalic acid (ODA) are dissolved in 50 g of pure ethanol in a 100 ml reactor with stirring while flushing gently with nitrogen. A 3.3 ethanolic solution containing 0.51 g (0.0044 mol) of 99% 2-methylpentane-1,5-diamine (MPMD) is added to this reactor over 5 minutes using a syringe driver. 10 ml of ethanol are used to rinse out the syringe driver. The stirred reaction medium is heated to 70° C. and maintained for 2 h 30. The polyimide salt formed precipitates and is recovered by complete evaporation of the ethanol at 60° C. under reduced pressure (300 mbar) and then dried at 45° C. under vacuum overnight. The salt is subsequently brought to 180° C. for 2 hours while flushing with nitrogen in order to obtain the polyimide. The polyimide is amorphous (no detection of melting point or of crystallization temperature) and exhibits a glass transition temperature of Tg=134.8° C.

It turns out that the PI MPMDODPA is amorphous and its Tg is less than 150° C. Thus, if it is stressed above its Tg, for example at 200° C., as is the case in an environment under an engine hood in a motor vehicle, it softens and loses its mechanical properties and thus cannot be used at this temperature.

Comparative Example 1: Preparation of the Polyimide PI 5PMA from a Tetraacid at 200° C.

2.192 g (0.0084 mol) of 97.5% pyromellitic acid (PMA) (Sigma-Aldrich) are dissolved in 70 g of pure ethanol in a 150 ml reactor with stirring and while flushing gently with nitrogen. A 5% ethanolic solution containing 1.0129 g (0.0086 mol) of 86.7% 1,5-pentanediamine (the impurity is water) is added to this reactor over 1 hour using a syringe driver. 10 ml of ethanol are used to rinse out the syringe driver. The stirred reaction medium is heated to 75° C. and maintained for 2 h. The polyimide 5PMA salt formed precipitates and is recovered by filtration under vacuum pressure and then dried at 45° C. under vacuum overnight. The salt powder is white and fine.

The salt is subsequently brought to 200° C. for 30 min while flushing with nitrogen in order to obtain the polyimide. A polyimide PI 5PMA is obtained which has the following thermal properties: M.p.=407° C. (ΔHf=21 J/g), Tc=391° C. and Tg=196° C. These performances are extremely high but it turns out that the PI 5PMA starts to decompose from 370° C. (1% loss in weight) and reaches 5' loss in weight at 439° C. Thus, the PI 5PMA starts decomposing before it starts melting: it is not possible to envisage employing it in the form of articles by remelting.

Comparative Example 2: Preparation of the Polyimide PI 12PMA from a Tetraacid at 200° C.

40 g (0.15 mol) of 94.9% pyromellitic acid (Sigma-Aldrich) and 2 liters of pure ethanol are introduced into a 5 l reactor. The reaction medium is stirred and heated to 70° C. while flushing gently with nitrogen. 30.5 g (0.15 mol) of 98% 1,12-diaminododecane (TCI Europe N.V.) are dissolved in 500 ml of pure ethanol in a 1 l round-bottom flask at ambient temperature. This solution is subsequently placed in a dropping funnel connected to the 5 l reactor and is added dropwise over 1 hour to the ethanolic solution of pyromellitic acid. The contact between the diamine and the pyromellitic acid brings about the formation of a salt which immediately precipitates with vigorous stirring. The reaction medium is kept vigorously stirred at 70° C. and under nitrogen for 3 h 30 min. The salt powder is recovered by filtration on a Bichner funnel and washed with ethanol, then ground and dried under vacuum at 50° C. overnight. The yield by weight is 95%. The powder is white and fine. The melting point of the salt is 260° C. The 12PMA salt powder is placed in a fluted round-bottom flask attached to a rotary evaporator and placed under gentle flushing with nitrogen. The pressure is equal to atmospheric pressure. The round-bottom flask is immersed in an oil bath at 200° C. and rotated for 8 hours. The PI 12PMA powder obtained is white and completely dry. The PI 12PMA powder has a melting point of 303° C. (enthalpy of fusion ΔHf=35 J/g), a crystallization temperature of 274° C. and a Tg=101° C. This PI 12PMA starts decomposing at 418° C. (1% loss in weight) and reaches 5% loss in weight at 451° C. Thus, the PI 12PMA is a semi-crystalline thermoplastic which can be shaped by remelting but for which the Tg=101° C. is low in comparison with very high performance polymers, such as PEEK, which limits its field of use in its vitreous state to less than 100° C.

The advantage is seen here of the examples of the invention, which make it possible to have semi-crystalline polyimides for which the Tg is very high, much greater than 150° C., while having a melting point compatible with the processes for the conversion of thermoplastics without an obvious deterioration in the properties.

Example 9: Preparation of PI MPMDPMA/Carbon Fabric Composite

A batch of 150 g of PI MPMDPMA polyimide blocked by 12-aminododecane with a relative viscosity of 1.85 prepared according to a process similar to that described in example 5 is used to prepare a PI MPMDPMA/carbon fabric thermoplastic composite.

Before use, the powder is dried at 90° C. under vacuum overnight.

The reinforcement used in this example is in the form of preforms made of carbon fabrics, cut to the dimensions required for the manufacture of sheets, that is to say 100× 150 mm. The reinforcing cloth used is a balanced fabric made of carbon fiber (0°-90°) originating from Hexcel, exhibiting a grammage of 200 g/m² (3K).

The composite parts are prepared by means of a force-controlled two-plate 100 tonne hydraulic press equipped with an induction heating mold (RocTool technology) and with cooling means (circulation of water). The metal mold has a cavity with dimensions of 150 mm×150 mm.

In order to produce a composite comprising 55% by volume of carbon fibers with the fabrics having a grammage of 200 g/m² (3K), a preform is prepared by stacking up carbon layers, each layer being dusted relatively homogeneously with polyimide powder. In the example under consideration, 10 carbon layers (200 g/m²) were used. The preform consisting of the stack of dusted layers is then introduced into the mold.

After introducing the preform and closing the mold under very low pressure, the temperature of the plates of the press is then raised to 355° C. in 91 seconds. A stationary phase is carried out at a very low pressure at 355° C. for 60 seconds. At the end of the stationary phase (60 seconds), a pressure is applied for 20 seconds: 30 bar jack. Cooling is carried out under pressure for 6 minutes 30 seconds: removal of the sheets from the mold at approximately 50° C.

The total cycle time is less than 10 minutes.

The sheets obtained of 2.4 mm. The composite articles according to the invention exhibit a very good surface appearance.

It is possible to obtain composite articles by using the polyimides according to the invention, in particular while carrying out extremely short manufacturing cycles.

The invention claimed is:

1. A salt composition, comprising:
   at least one ammonium carboxylate salt obtained from:
   (a) at least one aromatic compound comprising 2 anhydride functional groups and/or its carboxylic acid and/or ester derivatives selected from the group consisting of: pyromellitic anhydride, 3,3',4,4'-biphenyltetracarboxylic dianhydride, pyromellitic acid, 3,3',4,4'-biphenyltetracarboxylic acid and their mixtures; and
   (b) one or more aliphatic diamines, the amine functional groups of which are not covalently bonded to a carbon atom of an aromatic ring, in which said one or more aliphatic diamines are of formula (I) $NH_2$—R—$NH_2$ with R being a saturated aliphatic divalent hydrocarbon radical, the two amine functional groups of which are separated by 4 to 6 carbon atoms and 1 or 2 hydrogen atoms of the divalent radical of which are replaced by 1 or 2 methyl and/or ethyl groups; and wherein the one or more aliphatic diamines optionally further comprises at least one diamine of formula (II) $NH_2$—R'—$NH_2$ with R' being a saturated or unsaturated and aliphatic, cycloaliphatic or arylaliphatic divalent hydrocarbon radical, which optionally comprises heteroatoms; and
   at least one chain-limiting compound chosen from monoamines, monoacids or diacids in the α,β positions such that they can form an anhydride functional group by a dehydration reaction, wherein the at least one chain-limiting compound is added to a preformed ammonium carboxylate salt.

2. The salt composition as claimed in claim 1, characterized in that the diamine of formula (I) is selected from the group consisting of: 2-ethyltetramethylene-1,4-diamine, 2-methylpentamethylene-1,5-diamine or a mixture of these.

3. The salt composition as claimed in claim 1, characterized in that the diamine of formula (I) is 2-methylpentamethylene-1,5-diamine.

4. The salt composition as claimed in claim 1, characterized in that the chain-limiting compound is chosen from: 1-aminopentane, 1-aminohexane, 1-aminoheptane, 1-aminooctane, 1-aminononane, 1-aminodecane, 1-aminoundecane, 1-aminododecane, benzylamine, ortho-phthalic acid, acetic acid, propionic acid, benzoic acid, stearic acid or their mixtures.

5. A process for the manufacture of semi-aromatic thermoplastic (co)polyimide by polymerization of the salt composition as claimed in claim 1.

6. A method of manufacturing a semi-aromatic thermoplastic (co)polyimide, comprising:
   subjecting a salt composition as claimed in claim 1 to a melt polymerization or a solid-state polymerization.

7. A salt composition, comprising:
   at least one ammonium carboxylate salt obtained from:
   (a) at least one aromatic compound comprising 2 anhydride functional groups and/or its carboxylic acid and/or ester derivatives; and
   (b) one or more aliphatic diamines in which said one or more aliphatic diamines are of formula (I) $NH_2$—R—$NH_2$ with R being a saturated aliphatic divalent hydrocarbon radical, the two amine functional groups of which are separated by 4 to 6 carbon atoms and 1 or 2 hydrogen atoms of the divalent radical of which are replaced by 1 or 2 methyl and/or ethyl groups; and wherein the one or more aliphatic diamines optionally further comprises at least one diamine of formula (II) $NH_2$—R'—$NH_2$ with R' being a saturated or unsaturated and aliphatic, cycloaliphatic or arylaliphatic divalent hydrocarbon radical, which optionally comprises heteroatoms; and
   at least one chain-limiting compound chosen from a salt of monoamines, monoacids or diacids in the α,β positions such that they can form an anhydride functional group by a dehydration reaction, wherein the at least one chain-limiting compound is added during the formation of the at least one ammonium carboxylate salt.

* * * * *